(12) United States Patent
Matsumoto et al.

(10) Patent No.: US 9,873,104 B2
(45) Date of Patent: Jan. 23, 2018

(54) METHOD FOR PRODUCING POLYACRYLIC ACID (SALT)-BASED WATER-ABSORBING RESIN

(71) Applicant: NIPPON SHOKUBAI CO., LTD., Osaka-shi, Osaka (JP)

(72) Inventors: Satoshi Matsumoto, Himeji (JP); Shinichi Fujino, Himeji (JP); Kunihiko Ishizaki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 15/123,040

(22) PCT Filed: Mar. 3, 2015

(86) PCT No.: PCT/JP2015/056260
§ 371 (c)(1),
(2) Date: Sep. 1, 2016

(87) PCT Pub. No.: WO2015/133498
PCT Pub. Date: Sep. 11, 2015

(65) Prior Publication Data
US 2017/0216816 A1 Aug. 3, 2017

(30) Foreign Application Priority Data
Mar. 3, 2014 (JP) ................. 2014-040555

(51) Int. Cl.
| | | |
|---|---|---|
| *B01J 20/26* | (2006.01) | |
| *A61L 15/24* | (2006.01) | |
| *A61L 15/60* | (2006.01) | |
| *C08F 220/06* | (2006.01) | |
| *C08J 3/075* | (2006.01) | |
| *B01J 20/30* | (2006.01) | |

(52) U.S. Cl.
CPC .......... *B01J 20/267* (2013.01); *A61L 15/24* (2013.01); *A61L 15/60* (2013.01); *B01J 20/3021* (2013.01); *C08F 220/06* (2013.01); *C08J 3/075* (2013.01); *C08J 2333/02* (2013.01)

(58) Field of Classification Search
CPC ......... B01J 20/26; B01J 20/267; A61L 15/24; A61L 15/60
USPC ........................................ 502/402
See application file for complete search history.

(56) References Cited

U.S. PATENT DOCUMENTS

| | | |
|---|---|---|
| 5,118,719 A | 6/1992 | Lind |
| 6,136,873 A | 10/2000 | Hähnle et al. |
| 2005/0137546 A1 | 6/2005 | Joy et al. |
| 2006/0183828 A1 | 8/2006 | Dairoku et al. |
| 2009/0008220 A1 | 1/2009 | Hillebrecht et al. |
| 2010/0041550 A1 | 2/2010 | Riegel et al. |
| 2010/0268181 A1 | 10/2010 | Ziemer et al. |
| 2010/0273942 A1 | 10/2010 | Funk et al. |
| 2011/0015288 A1 | 1/2011 | Ranft et al. |
| 2011/0118430 A1 | 5/2011 | Funk et al. |

FOREIGN PATENT DOCUMENTS

| | | |
|---|---|---|
| JP | A-2008-156491 | 7/2008 |
| JP | A-2010-516883 | 5/2010 |
| JP | A-2013-076073 | 4/2013 |

OTHER PUBLICATIONS

Modern Superabsorbent Polymer Technology (1998), edited by Fredric L. Buchholz and Andrew T. Graham, VILEY-VCH p. 69-103.
International Search Report issued in PCT Application No. PCT/JP2015/056260.
Notification of Transmittal of the International Preliminary Report on Patentability dated Sep. 6, 2016, which issued in the counterpart PCT Application No. PCT/JP2015/056260, including English translation.

*Primary Examiner* — Edward Johnson
(74) *Attorney, Agent, or Firm* — Dickinson Wright, PLLC

(57) ABSTRACT

To provide a method for producing a water-absorbing resin by which problems caused by addition of a particulate additive or water-absorbing resin fine powder can be prevented and a water-absorbing resin having high physical properties can be stably and efficiently obtained.
A method for producing a polyacrylic acid (salt)-based water-absorbing resin, the method including: an aqueous monomer solution preparation step for preparing an aqueous solution containing a monomer having an acrylic acid (salt) as a main component; a polymerization step for polymerizing the monomer to obtain a hydrogel-forming crosslinked polymer; and a drying step for drying the hydrogel-forming crosslinked polymer to obtain a dry polymer, wherein the method further includes an adding step for adding a particulate additive to the aqueous monomer solution and/or the hydrogel-forming crosslinked polymer, and in the adding step, an oxygen concentration in an ambient atmosphere of the particulate additive is set to 5% by volume or less.

14 Claims, 2 Drawing Sheets

METHOD FOR PRODUCING POLYACRYLIC ACID (SALT)-BASED WATER-ABSORBING RESIN

BACKGROUND ART

Technical Field

The present invention relates to a method for producing a polyacrylic acid (salt)-based water-absorbing resin.

Related Art

A water-absorbing resin (SAP/Super Absorbent Polymer) is a polymer gelling agent having water swellable property and water insoluble property and has been widely used as absorbing agents for hygiene products such as disposable diapers and sanitary napkins, agriculture/horticulture water retention agents, industrial waterproofing materials and the like.

The water-absorbing resin is produced from various kinds of monomers or hydrophilic polymers as a raw material. In particular, a polyacrylic acid (salt)-based water-absorbing resin using as a monomer an acrylic acid and/or a salt thereof has high absorbent performance, and thus most widely produced industrially.

The water-absorbing resin is produced as a particulate product through various steps such as polymerization, drying, crushing, classification, and surface crosslinking (Non-Patent Literature 1). Further, as disposable diapers, a primary application of the water-absorbing resin, become more high-performance, more functionalities (physical properties) are needed. Specifically, in addition to fluid retention capacity, examples of such functionalities (physical properties) include gel strength, water soluble component, water absorption speed, fluid retention capacity under pressure, liquid permeability, particle size distribution, urine resistance, antibacterial property, impact resistance (damage resistance), powder fluidity, deodorant property, anti-coloring property (whiteness), and low dustiness.

Addition of an additive is mentioned as a method for providing these functions (physical properties).

As a technique of adding an additive, there are techniques of adding an additive to a polymerization reaction vessel using a screw conveyor (Patent Literatures 1 and 2). In addition, techniques of adding a reducing agent or an oxidizer in order to reduce residual monomers (Patent Literatures 3 and 4) are proposed.

Furthermore, among the aforementioned functions (physical properties), water absorption speed is considered particularly important, and as a technique of improving the water absorption speed, foaming polymerization and the like (Patent Literatures 5 to 9) are proposed.

CITATION LIST

Patent Literatures

Patent Literature 1: US 2009/0008220
Patent Literature 2: US 2010/0273942
Patent Literature 3: US 2011/0118430
Patent Literature 4: US 2006/0183828
Patent Literature 5: U.S. Pat. No. 5,118,719
Patent Literature 6: US 2005/0137546
Patent Literature 7: U.S. Pat. No. 6,136,873
Patent Literature 8: US 2010/0268181
Patent Literature 9: US 2011/0015288

Non-Patent Literature

Non-Patent Literature 1: Modern Superabsorbent Polymer Technology (1998), p. 69-103

SUMMARY OF INVENTION

However, the aforementioned related arts have a problem that the residual monomer amount in the water-absorbing resin to be obtained is increased. In addition, when foaming polymerization is employed in order to improve the water absorption speed, the related arts have a problem that residual monomers are increased.

In this regard, a problem to be solved by the present invention is to provide a method for producing a water-absorbing resin that can prevent problems caused by addition of an additive and can stably and efficiently obtain water-absorbing resin having high physical properties. That is, a problem to be solved by the present invention is to suppress the residual monomer amount in a water-absorbing resin to be obtained and to stably provide a water-absorbing resin having a high water absorption speed and high physical properties.

As a result of intensive studies which the present inventors conducted in order to solve the above-described problems, the present invention has been completed and found that, when a particulate additive is added, lowering an oxygen concentration of an ambient atmosphere of a particulate additive as much as possible can suppress an increase of residual monomers, thereby efficiently and stably yielding a water-absorbing resin with better physical properties.

In order to achieve at least one of the aforementioned objects, a method for producing a polyacrylic acid (salt)-based water-absorbing resin according to an aspect of the present invention has the following features. That is, the present invention is a method for producing a polyacrylic acid (salt)-based water-absorbing resin, the method including: an aqueous monomer solution preparation step for preparing an aqueous solution containing a monomer having acrylic acid (salt) as a main component; a polymerization step for polymerizing the monomer to obtain a hydrogel-forming crosslinked polymer; and a drying step for drying the hydrogel-forming crosslinked polymer to obtain a dry polymer, and the method further including an adding step for adding a particulate additive to the aqueous monomer solution and/or the hydrogel-forming crosslinked polymer, and in the adding step, an oxygen concentration in an ambient atmosphere of the particulate additive is set to 5% by volume or less.

DESCRIPTION OF EMBODIMENTS

Figure 1:
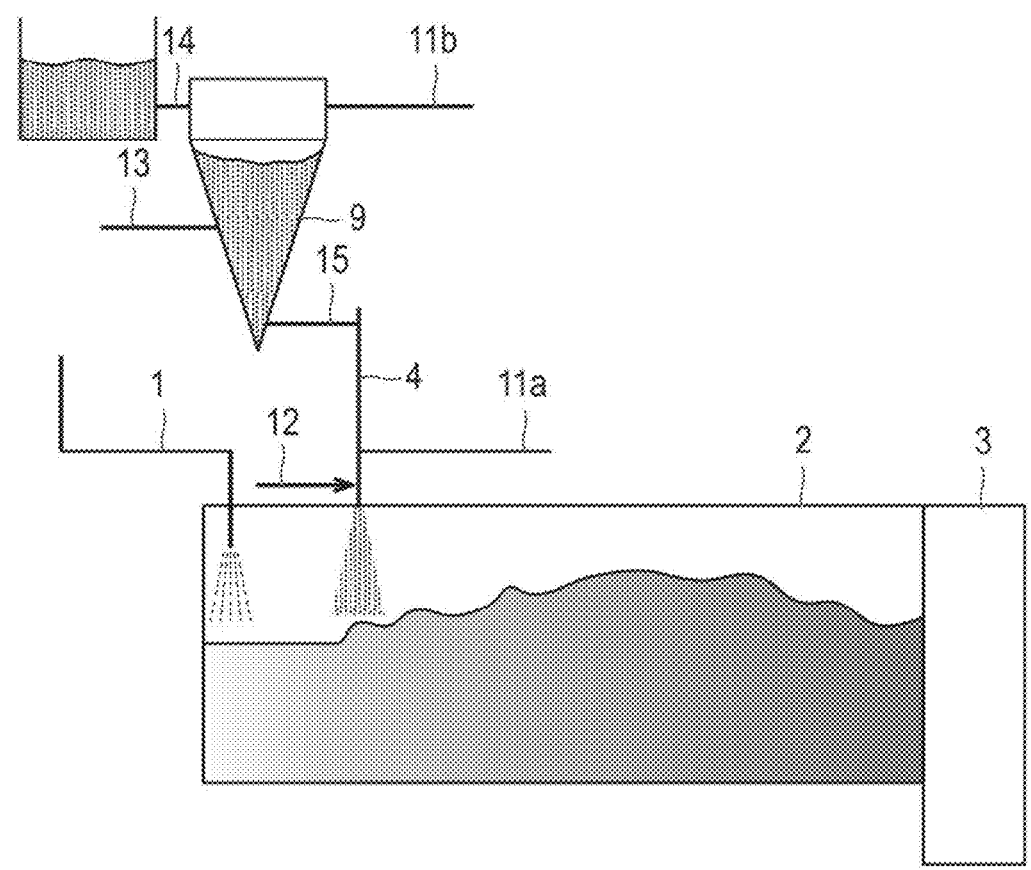
FIG. 1 is a diagram of an apparatus for producing a polyacrylic acid (salt)-based water-absorbing resin described in Example of the present invention.

Hereinafter, a method for producing a polyacrylic acid (salt)-based water-absorbing resin according to the present invention will be described in detail. However, the scope of the present invention is not restricted to the following descriptions, and those other than the following examples can be properly modified and carried out to an extent in which a gist of the present invention is not impaired. Specifically, the present invention is not limited to each of the following embodiments, and various modifications can be made within a scope shown by the claims and embodiments carried out by properly combining each technical means disclosed with different embodiments are also included within the technical scope of the present invention.

[1] Definition of Terms (1-1) "Water-Absorbing Resin"

In the present invention, a "water-absorbing resin" indicates a polymer gelling agent having water swellable property and water insoluble property, and satisfies the following physical properties. That is, the water-absorbing resin indicates a polymer gelling agent satisfying physical properties in which for a "water swellable property," CRC as defined in ERT 441.2-02 is 5 g/g or more, and for a "water insoluble property," Ext as defined in ERT 470.2-02 is 50% by weight or less.

Further, the water-absorbing resin in the present invention may include an intermediate produced in the process of producing the water-absorbing resin (for example, a hydrogel-forming crosslinked polymer after polymerization, a dry polymer after drying, or water-absorbing resin powder before surface crosslinking) and is not limited to a final product, and thus the foregoing water-absorbing resin composition and all the above together may be collectively referred to as "water-absorbing resin." A form of the water-absorbing resin may be in sheet, fiber, film, particulate, gel and the like, but according to the present invention, the water-absorbing resin in a particulate form is preferable.

(1-2) "Polyacrylic Acid (Salt)"

"Polyacrylic acid (salt)" in the present invention indicates a polyacrylic acid and/or a salt thereof, and means a polymer containing as a main component an acrylic acid and/or a salt thereof (hereinafter, referred to as "acrylic acid (salt)") as a repeating unit and optionally contains graft components.

The foregoing "main component" means that an amount used (included amount) of the acrylic acid (salt) is usually 50 to 100% by mol, preferably 70 to 100% by mol, more preferably 90 to 100% by mol, still more preferably substantially 100% by mol with respect to the entire monomer (excluding an internal crosslinking agent) used in polymerization.

(1-3) "EDANA" and "ERT"

"EDANA" is an abbreviation for European Disposables and Nonwovens Associations, and "ERT" is an abbreviation for EDANA Recommended Test Methods, which is the measurement methods for water-absorbing resins under the European standards (essentially the world standards). In the present invention, the physical properties of the water-absorbing resin are measured according to the original ERT (known literature, revised in 2002), unless otherwise indicated.

(1-3-1) "Crc" (Ert 441.2-02)

"CRC" is an abbreviation for Centrifuge Retention Capacity and means a fluid retention capacity without pressure (also referred to as "fluid retention capacity") of the water-absorbing resin.

Specifically, CRC means a fluid retention capacity (unit; g/g) obtained after 0.2 g of a water-absorbing resin is put in a nonwoven fabric bag, and then immersed in a large excess of 0.9% by weight of aqueous sodium chloride solution for 30 minutes for free swelling, and then the water-absorbing resin is dehydrated in a centrifuge (250 G).

(1-3-2) "AAP" (ERT 442.2-02)

"AAP" is an abbreviation for Absorption Against Pressure, and means a fluid retention capacity under pressure of the water-absorbing resin.

Specifically, AAP means a fluid retention capacity (unit; g/g) obtained after 0.9 g of a water-absorbing resin is allowed to swell in a large excess of 0.9% by weight of aqueous sodium chloride solution for 1 hour under a load of 2.06 kPa (21 g/cm$^2$, 0.3 psi). This measurement can also be taken with a load condition being changed to 4.83 kPa (49 g/cm$^2$, 0.7 psi). AAP is listed as Absorption Under Pressure in ERT 442.2-02, but it is substantively the same.

(1-3-3) "PSD" (ERT 420.2-02)

"PSD" is an abbreviation for Particle Size Distribution and means a particle size distribution in the water-absorbing resin measured by sieving classification.

A weight average particle diameter (D50) and a logarithmic standard deviation (sz) of the particle size distribution are measured by methods same as "(3) Mass-Average Particle Diameter (D50) and Logarithmic Standard Deviation (sz) of Particle Diameter Distribution" which is described in U.S. Pat. No. 7,638,570.

(1-3-4) "Ext" (ERT 470.2-02)

"Ext" is an abbreviation for Extractables and means a water soluble component (amount of water soluble contents) of the water-absorbing resin.

Specifically, Ext is an amount of a dissolved polymer (unit; % by weight), which is obtained after 1.0 g of a water-absorbing resin is added to 200 ml of 0.9% by weight of aqueous sodium chloride solution and stirred for 16 hours at 500 rpm. The measurement for the amount of the dissolved polymer is taken by pH titration.

(1-3-5) "Moisture Content" (ERT 430.2-02)

"Moisture Content" means a moisture content of the water-absorbing resin.

Specifically, a moisture content is a value (unit; % by weight) calculated based upon an amount lost from drying after 4.0 g of a water-absorbing resin is dried for 3 hours at 105 C. The amount of the water-absorbing resin can be changed to 1.0 g, and the drying temperature can also be changed to 180 C.

(1-3-6) "Residual Monomers" (ERT 410.2-02)

"Residual Monomers" means an amount of monomers remained in a water-absorbing resin (hereinafter, referred to as "residual monomers").

Specifically, Residual Monomers is an amount of a dissolved residual monomer (unit; ppm) obtained after 1.0 g of a water-absorbing resin is added to 200 ml of 0.9% by weight of aqueous sodium chloride solution and stirred for 1 hour at 500 rpm. The measurement of the amount of the dissolved residual monomer is taken by high performance liquid chromatography (HPLC).

(1-4) Others

In the present specification, "X to Y" representing a range means "equal to or more than X and equal to or less than Y." Further, unless otherwise specified, "ppm" means "ppm by weight" or "ppm by mass." Furthermore, "weight" and "mass," "part by weight" and "part by mass," and "% by weight" and "% by mass" are treated as synonymous, respectively. In addition, the expression " . . . acid (salt)" means " . . . acid and/or a salt thereof."

[2] Method for Producing Polyacrylic Acid (Salt)-Based Water-Absorbing Resin

The present invention relates to a method for producing a polyacrylic acid (salt)-based water-absorbing resin, the method including: an aqueous monomer solution preparation step for preparing an aqueous solution containing a monomer having acrylic acid (salt) as a main component; a polymerization step for polymerizing the monomer to obtain a hydrogel-forming crosslinked polymer; and a drying step for drying the hydrogel-forming crosslinked polymer to obtain a dry polymer, and the method further includes an adding step for adding a particulate additive to the aqueous monomer solution and/or the hydrogel-forming crosslinked polymer, and in the adding step, an oxygen concentration in an ambient atmosphere of the particulate additive is set to 5% by volume or less.

With such a configuration, the residual monomer in the water-absorbing resin after drying can be suppressed, and in addition, absorbent performance can be stabilized.

Hereinafter, a method for producing a polyacrylic acid (salt)-based water-absorbing resin according to the present invention will be described.

(2-1) Aqueous Monomer Solution Preparation Step

This step is a step for preparing an aqueous solution containing a monomer with an acrylic acid (salt) as its main component (hereinafter, referred to as "aqueous monomer solution"). A slurry of the monomer can also be used as long as the absorbent performance of the water-absorbing resin to be obtained is not lowered. For simplicity, an aqueous monomer solution is discussed herein.

The foregoing "main component" indicates that an amount of the acrylic acid (salt) included (or used) is usually 50% by mol or more, preferably 70% by mol or more, and more preferably 90% by mol or more (the upper limit is 100% by mol) with respect to the entire monomer (excluding an internal crosslinking agent) content provided for the polymerization reaction of the water-absorbing resin.

(Acrylic Acid)

In the present invention, from the viewpoint of physical properties and productivity of the water-absorbing resin to be obtained, an acrylic acid and/or a salt thereof (hereinafter, referred to as "acrylic acid (salt)") is used as a monomer.

As to the foregoing "acrylic acid," acrylic acid, which is well-known as containing a minor component such as a polymerization inhibitor or some impurities, can be used. The polymerization inhibitor is not particularly limited, but it is preferably a methoxyphenol and the family thereof, or more preferably p-methoxyphenol and the family thereof. Further, the amount used is preferably 200 ppm or less, more preferably 10 to 160 ppm, and still more preferably 20 to 100 ppm from the viewpoint of polymerization property of the acrylic acid and color of the water-absorbing resin. Further, as for the impurities in the acrylic acid, compounds described in US Patent Publication No. 2008/0161512 are also applied to the present invention.

The foregoing "acrylic acid salt" is obtained by neutralizing acrylic acid with the following basic compounds. An acrylic acid salt may be ones that are commercially available (for example, sodium acrylate) or may be obtained through neutralization in a production plant for a water-absorbing resin.

(Basic Compound)

In the present invention, "basic compound" includes, for example, a commercially available aqueous sodium hydroxide solution or the like.

Some examples of the basic compound include alkali metal carbonate or hydrogen carbonate, alkali metal hydroxide, ammonia, and organic amine. Among them, from the viewpoint of physical properties of the water-absorbing resin to be obtained, a strongly basic compound is desirable. That is, alkali metal hydroxide such as sodium hydroxide, potassium hydroxide, or lithium hydroxide is preferable, and sodium hydroxide is more preferable.

Further, in the present invention, neutralization may be performed with a basic compound containing polycations in an extremely small amount (for example, 5% by mol with respect to acrylic acid).

(Neutralization)

In the present invention, in order to obtain the acrylic acid salt, acrylic acid can be neutralized with a basic compound. This neutralization may be selected from either types of neutralization as follows or may be both: neutralization of acrylic acid (that is, before polymerization) and/or neutralization of a hydrogel-forming crosslinked polymer obtained by crosslinking and polymerizing acrylic acid (that is, after polymerization) (hereinafter referred to as "post-neutralization").

Further, the neutralization may be carried out with a continuous method or a batch method and there is no limitation on neutralization method; however, from the viewpoint of production efficiency, a continuous method is preferable.

Regarding neutralization conditions including an apparatus for neutralization, neutralization temperature and retention time, such conditions described in WO 2009/123197 and US Patent Publication No. 2008/0194863 are also applied to the present invention.

The rate of neutralization according to the present invention is preferably 10 to 90% by mol, more preferably 40 to 85% by mol, still more preferably 50 to 80% by mol, and particularly preferably 60 to 78% by mol with respect to acid groups in a monomer. In a case where the rate of neutralization is less than 10% by mol, fluid retention capacity may be significantly decreased. On the other hand, when the rate of neutralization is more than 90% by mol, a water-absorbing resin having high fluid retention capacity under pressure may not be obtained.

The same applies to the rate of neutralization in the case of the post-neutralization. Further, the above-described rate of neutralization is also applied to the rate of neutralization of the water-absorbing resin as a final product.

(Other Monomers)

In the present invention, as "other monomers," the water-absorbing resin can be produced by using compounds described in US Patent Publication No. 2005/0215734 (however, an acrylic acid is excluded) together with the foregoing acrylic acid (salt) in parallel. In the water-absorbing resin obtained by the producing method according to the present invention, a water-absorbing resin containing a water-soluble or hydrophobic unsaturated monomer as a copolymerization component is also included.

(Internal Crosslinking Agent)

As the internal crosslinking agent which may be used in the present invention, compounds described in U.S. Pat. No. 6,241,928 are also applied to the present invention. Among these, in consideration of reactivity, one or two or more kinds of compound are selected.

Further, from the viewpoint of absorbent performance or the like of the water-absorbing resin to be obtained, as an internal crosslinking agent, a compound having two or more polymerizable unsaturated groups is preferably used, a compound that is thermally decomposed at a later-described drying temperature is more preferably used, and a compound that has two or more of polymerizable unsaturated groups having a (poly)alkylene glycol structural unit is still more preferably used.

As the polymerizable unsaturated group, an allyl group or a (meth)acrylate group is preferably mentioned and a (meth) acrylate group is more preferably mentioned. In addition, as the (poly)alkylene glycol structural unit, polyethylene glycol is preferable, and n number is preferably 1 to 100 and more preferably 6 to 50.

An amount of the internal crosslinking agent used is preferably 0.005 to 2% by mol, more preferably 0.01 to 1% by mol, and still more preferably 0.05 to 0.5% by mol with respect to the entire monomer. When the amount used is set to be in the above range, a desired water-absorbing resin may be obtained.

In the present invention, from the viewpoint of physical properties such as fluid retention capacity under pressure, it is preferable to employ a method in which a predetermined amount of the internal crosslinking agent is added to the aqueous monomer solution in advance, and then crosslinking reaction is carried out concurrently with polymerization. On the other hand, in addition to the above method, it is also possible to employ a method in which an internal crosslinking agent is added during polymerization or after polymerization and then crosslinking is carried out, a method for radical crosslinking using a radical polymerization initiator, a method for radiation crosslinking using active energy rays such as electron rays or ultraviolet rays, or the like. Further, these methods can be used in combination.

Further, in a case where an internal crosslinking agent is a compound having two or more polymerizable unsaturated groups, a polymerization inhibitor is usually contained in the internal crosslinking agent. The polymerization inhibitor is preferably the same as the polymerization inhibitor contained in the acrylic acid. Specifically, the polymerization inhibitor is preferably phenols or the resembling structure thereof, more preferably methoxyphenols or the resembling structure thereof, and still more preferably p-methoxyphenols or the resembling structure thereof.

From the viewpoint of polymerization properties of the aqueous monomer solution and color of the water-absorbing resin, the content (ppm) of the polymerization inhibitor contained in the internal crosslinking agent may be the same as the content (ppm) thereof in the acrylic acid; however, since the used amount of the internal crosslinking agent is extremely small, the content (ppm) of the polymerization inhibitor contained in the internal crosslinking agent is preferably higher than the content (ppm) thereof in the acrylic acid. The reason for this is that when the internal crosslinking agent is used in a solution form, stability is lowered, and there are many cases where the internal crosslinking agent is used in a solution form from the viewpoint of handleability.

(Concentration of Monomer Component)

In this step, each substance described above is added when an aqueous monomer solution is prepared. The concentration of the monomer components in the aqueous monomer solution (hereinafter, referred to as "monomer concentration" in some cases) is not particularly limited; however, from the viewpoint of physical properties and productivity of the water-absorbing resin, the monomer concentration is preferably 10 to 80% by weight, more preferably 20 to 75% by weight, and still more preferably 30 to 70% by weight.

Furthermore, in a case where aqueous solution polymerization or reversed phase suspension polymerization is employed, a solvent other than water can be used in combination, as necessary. In this case, the type of the solvent is not particularly limited.

The foregoing "concentration of monomer component" indicates the value which is obtained according to the following formula (1), and the weights of the graft component or water-absorbing resin, and a hydrophobic solvent in the reversed phase suspension polymerization are not included in the weight of the aqueous monomer solution.

[Math. 1]

$$\text{Concentration of monomer component (\% by weight)} = (\text{Weight of monomer component})/(\text{Weight of aqueous monomer solution}) \cdot 100 \quad (1)$$

Further, a polymerization inhibitor incorporated from the acrylic acid is contained in the aqueous monomer solution. As the polymerization inhibitor, methoxyphenols or the resembling structure thereof are preferably mentioned and p-methoxyphenols or the resembling structure thereof are more preferably mentioned. The concentration of the polymerization inhibitor is preferably 200 ppm or less, more preferably 10 to 160 ppm, and still more preferably 20 to 100 ppm.

(2-2) Polymerization Step

This step is a step for polymerizing the aqueous monomer solution, which contains a monomer having an acrylic acid (salt) as a main component, obtained in the aqueous monomer solution preparation step to obtain a hydrogel-forming crosslinked polymer.

(Polymerization Initiator)

Since a polymerization initiator used in the present invention is appropriately selected in accordance with polymerization form or the like, the polymerization initiator is not particularly limited. Examples of the polymerization initiator include a pyrolytic polymerization initiator, a photolytic polymerization initiator, and a redox polymerization initiator in which a reducing agent for facilitating decomposition of any of those polymerization initiators is used in combination. Specifically, one or two or more kinds of the polymerization initiators disclosed in U.S. Pat. No. 7,265,190 are used. From the viewpoint of handleability of the polymerization initiator and physical properties of the water-absorbing resin, peroxides or azo compounds are preferably used, peroxides are more preferably used, and persulfates are still more preferably used. As a salt, sodium, potassium, or the like is preferable.

The amount of the polymerization initiator used is preferably 0.001 to 1% by mol and more preferably 0.001 to 0.5% by mol per the monomer. Further, the used amount of the reducing agent is preferably 0.0001 to 0.02% by mol with respect to the monomer.

Polymerization reaction can be carried out by irradiation of active energy rays such as radiation rays, electron rays, or ultraviolet rays instead of using the polymerization initiator. These active energy rays and the polymerization initiator may be used in combination.

(Polymerization Form)

The polymerization form employed in the present invention is not particularly limited. From the viewpoint of water absorbent property, ease of controlling polymerization, and the like, spray drop polymerization, aqueous solution polymerization, or reversed phase suspension polymerization is preferably mentioned, aqueous solution polymerization or reversed phase suspension polymerization is more preferably mentioned, and aqueous solution polymerization is still more preferably mentioned. Among these aqueous solution polymerizations, continuous aqueous solution polymerization is particularly preferable, and from the viewpoint of mixing properties of the following additives, continuous kneader polymerization is most preferable.

As a specific polymerization form, examples of continuous belt polymerization are disclosed in U.S. Pat. No. 4,893,999, U.S. Pat. No. 6,241,928, and US 2005/0215734, and examples of continuous kneader polymerization are disclosed in U.S. Pat. No. 6,987,151 and U.S. Pat. No. 6,710,141. By employing these continuous aqueous solution polymerizations, efficiency in producing the water-absorbing resin is improved.

Further, preferred examples of the continuous aqueous solution polymerization include "high-temperature initiating polymerization" and "high concentration polymerization." The "high-temperature initiating polymerization" is a polymerization form in which the polymerization is started when a temperature of the aqueous monomer solution is preferably 30 C or higher, more preferably 35 C or higher, still more preferably 40 C or higher, and particularly preferably 50 C or higher (and an upper limit is a boiling point). The "high concentration polymerization" is a polymerization form in which the polymerization is carried out with a concentration of preferably 30% by weight or more, more preferably 35% by weight or more, still more preferably 40% by weight or more, and particularly preferably 45% by weight or more (and an upper limit is a saturating concentration). These polymerization forms can be used in combination. When the polymerization forms are used in combination in this way, a water-absorbing resin excellent in fluid retention capacity under pressure and water absorption speed is easily obtained.

Further, in the present invention, polymerization can be carried out under an air atmosphere. From the viewpoint of shortening the polymerization time and decreasing the water soluble component of the water-absorbing resin to be obtained, polymerization is preferably carried out under an atmosphere of inert gas such as nitrogen or argon. In this case, for example, it is preferable to control an oxygen concentration to 1% by volume or less. By doing so, it is possible to obtain a water-absorbing resin in which the residual monomer is small. It is preferable that dissolved oxygen in the aqueous monomer solution be substituted by inert gas (for example, dissolved oxygen; less than 1 mg/l). By doing so, it is possible to obtain a water-absorbing resin in which the residual monomer is small. The pressure of a polymerization apparatus may be reduced by evacuation of air.

Further, in the present invention, the concentration of solids content may be increased during the polymerization. The degree of increase in solids content as an indicator of an increase in concentration of solids content is defined by the following formula (2). The degree of increase in concentration of solids content is preferably 1% by weight or more and more preferably 2% by weight or more.

[Math. 2]

Degree of increase in solids content (% by weight)= (Concentration of solids content in hydrogel after polymerization (% by weight))−(Concentration of solids content in aqueous monomer solution (% by weight))    (2)

Meanwhile, the concentration of solids content in the aqueous monomer solution is a value obtained by the following formula (3) and the components in a polymerization system include an aqueous monomer solution, a graft component, a water-absorbing resin, and other solid matters (for example, water insoluble fine particles), and a hydrophobic solvent in reversed phase suspension polymerization is not included therein.

[Math. 3]

Concentration of solids content in aqueous monomer solution (% by weight)={Weight of (monomer component+graft component+water-absorbing resin+other solid matters)}/(Weight of components in polymerization system)·100    (3)

Further, in the present invention, it is also possible to employ foaming polymerization which is carried out by dispersing gas bubbles (in particular, the inert gas described above, or the like) in the aqueous monomer solution. Since the water-absorbing resin obtained in the foaming polymerization has gas bubbles therein and the specific surface area increases, a water absorption speed (FSR) is improved. The water absorption speed (FSR) is preferably 0.25 g/g/s or more, and when the water absorption speed is set to this value or more, the water-absorbing resin is advantageous for use of the absorbent material.

Further, since gas bubbles are contained in the water-absorbing resin obtained by the foaming polymerization, the generation amount of fine powder is more than that of a general water-absorbing resin not containing gas bubbles. Therefore, the present invention is more preferably employed. That is, when there is a large amount of gas bubbles, the thickness of the resin between the gas bubbles is decreased. Thus, a crushed product having a predetermined size or more may not be obtained at the time of crushing or the mechanical strength of the gas bubble portion is weak so that fine powder may be generated by damage after being crushed. As the amount of fine powder to be recovered increases, the amount of air incorporated also increases according to an increase in amount of fine powder. In an embodiment of the present invention, in a case where fine powder is recovered to be used as a particulate additive, treatment for adjusting the oxygen concentration to a specific value or less is carried out in the present invention, and thus the above-described problem can be solved.

After producing a hydrogel, from the viewpoint of reducing the residual monomer, the hydrogel may be aged for a certain time.

(2-3) Gel-Crushing Step

This step is a step for gel-crushing the "hydrogel" obtained in the polymerization step by, for example, using a screw extruder such as a kneader or a meat chopper or a gel-crusher such as a cutter mill to obtain particles of hydrogel (hereinafter, referred to as "particulate hydrogel"). Therefore, generally, the gel-crushing step is performed after the polymerization step.

In a case where the polymerization step is a kneader polymerization, the polymerization step and the gel-crushing step are carried out concurrently. Furthermore, in a case where the particulate hydrogel is obtained directly through a polymerization process such as gas phase polymerization or reversed phase suspension polymerization, the gel-crushing step may not be carried out.

Regarding gel-crushing conditions and embodiments other than those described above, the content disclosed in WO 2011/126079 is preferably applied to the present invention.

(2-4) Step for Adding Particulate Additive

This step is a step for adding the following particulate additive to the aqueous monomer solution and/or the hydrogel-forming crosslinked polymer. Since a product obtained by gel-crushing the hydrogel-forming crosslinked polymer is the "particulate hydrogel," the embodiment of adding the particulate additive to the "particulate hydrogel" is also included in the embodiment of adding the particulate additive to the "hydrogel-forming crosslinked polymer."

The particulate additive partially overlaps the additives described in (2-8) Remoistening Step and (2-9) Step for Adding Other Additives; however, the addition point is different. Thus, only an additive added in any of (2-1) Aqueous Monomer Solution Preparation Step, (2-2) Polymerization Step, and (2-3) Gel-Crushing Step is referred to as "particulate additive."

(Particulate Additive)

In the present invention, the particulate additive is not particularly limited as long as it is particulate and solid. From the viewpoint of improving physical properties of the water-absorbing resin and improving handleability, an inorganic compound, an organic compound, or a mixture thereof is mentioned.

The preferable amount of the particulate additive used varies depending on the type of particulate additive and is not particularly limited, but from the viewpoint of physical properties of the water-absorbing resin to be obtained, the preferable amount may be the amount as described below per 100 parts by weight of the monomer in the aqueous monomer solution. Although in a case where the particulate additive is added to the hydrogel-forming crosslinked polymer, the amount of the particulate additive used can be calculated from the monomer used for obtaining the hydrogel-forming crosslinked polymer. In addition, if the amount of the particulate additive used increases, the amount of air incorporated also increases according to an increase in amount of particulate additive. However, treatment for adjusting the oxygen concentration to a specific value or less is carried out in the present invention, and thus the above-described problem can be solved. Therefore, when the total amount of the particulate water-absorbing agent used is preferably set to 1% by weight or more, the effect of the present invention is further magnified.

First, some examples of the particulate additive will be described.

Specific examples of the inorganic compound include inorganic particles of clay mineral such as silica (silicon dioxide), titanium oxide, alumina, talc, zeolite, montmorillonite, hydrotalcite, kaolin, or smectite, water insoluble metallic phosphate, metallic carbonate, an inorganic reducing agent, and carbonate.

The particle diameter of the inorganic particles varies depending on each compound and is not particularly limited. From the viewpoint of achieving handleability of the inorganic particles and maximizing the effect to be provided to the water-absorbing resin, the particle diameter is preferably 0.1 to 4000 mm and more preferably 0.5 to 1000 mm. The particle diameter can be measured by sieve classification in a case where the particle diameter is 100 mm or more, and the particle diameter can be measured by a laser type particle size measuring machine in a case where the particle diameter is less than 100 mm.

In an embodiment of the present invention, the particulate additive preferably contains the inorganic particles described above. In this case, the inorganic particles content is preferably 0.01 to 5 parts by weight, more preferably 0.02 to 2 parts by weight, and still more preferably 0.05 to 1 parts by weight per 100 parts by weight of monomer in the aqueous monomer solution. Therefore, according to a preferred embodiment of the present invention, the particulate additive contains 0.01 to 5 parts by weight of inorganic particles per 100 parts by weight of monomer in the aqueous monomer solution.

Further, specific examples of the organic compound include fatty acid that is solid at normal temperature and has 10 to 20 carbon atoms (a so-called fatty acid salt such as metal soap), fatty acid ester, an azo compound, an aminocarboxylic acid-based or phosphoric acid-based chelating agent, an organic reducing agent, a chain transfer agent, a water soluble polymer, and water-absorbing resin fine powder.

The particularly preferred embodiment of the present invention is also characterized in that an organic compound (in particular, "water-absorbing resin fine powder"), which has not been focused as an additive in the related art, is used as an additive for improving physical properties such as water absorption speed and the oxygen concentration in an ambient atmosphere of the additive is set to a specific value or less.

In this way, when the organic compound (in particular, "water-absorbing resin fine powder"), which has not been focused as an additive in the related art, is used as an additive and the oxygen concentration in an ambient atmosphere of the additive is set to a specific value or less, it is possible to achieve unexpected effects that the residual monomer amount in the water-absorbing resin to be obtained is suppressed and a water-absorbing resin having high physical properties in which the water absorption speed is higher can be stably provided.

The used amount of the organic compound varies depending on the types of compounds to be added and is not particularly limited. For example, in the case of fatty acid that is solid at normal temperature and has 10 to 20 carbon atoms (a so-called fatty acid salt such as metal soap), and fatty acid ester, the used amount is more than 0 parts by weight, preferably 10 parts by weight or less, and more preferably 5 parts by weight or less. In addition, in the case of an azo compound, an aminocarboxylic acid-based or phosphoric acid-based chelating agent, an organic reducing agent, and a chain transfer agent, the used amount is more than 0 parts by weight, preferably 5 parts by weight or less, and more preferably 1 parts by weight or less. Furthermore, in the case of a water soluble polymer, the used amount is more than 0 parts by weight, preferably 50 parts by weight or less, and more preferably 30 parts by weight or less per 100 parts by weight of the monomer in the aqueous monomer solution.

In a case where the water soluble polymer or the water-absorbing resin fine powder is used as a particulate additive, a graft polymer or a water-absorbing resin composition (for example, a starch-acrylic acid polymer or a PVA-acrylic acid polymer) is obtained. In the present invention, these polymers and the water-absorbing resin composition are also included in the category of the polyacrylic acid (salt)-based water-absorbing resin.

In the present invention, the particulate additive preferably includes the water-absorbing resin fine powder. In this case, the water-absorbing resin fine powder content is usually more than 0 parts by weight, preferably 50 parts by weight or less, preferably 1 to 30 parts by weight, more preferably 2 to 25 parts by weight, still more preferably 5 to 20 parts by weight, particularly preferably 7 to 20 parts by weight, and most preferably 9 to 20 parts by weight per 100 parts by weight of the monomer in the aqueous monomer solution.

When the used amount is less than 1 part by weight, the effect of the present invention is not exhibited. On the other hand, when the used amount is more than 30 parts by weight, the generation amount of fine powder increases to cause deterioration of physical properties, which is not preferable.

According to the preferred embodiment of the present invention, the particulate additive contains 1 to 30 parts by weight of water-absorbing resin fine powder per 100 parts by weight of the monomer in the aqueous monomer solution. The water-absorbing resin fine powder can be produced separately from the water-absorbing resin of the present invention, and may be generated at the time of producing the water-absorbing resin of the present invention. In this way, not only physical properties of the water-absorbing resin to be obtained can be improved but also the water-absorbing resin fine powder can be reused.

Further, the water-absorbing resin fine powder indicates a water-absorbing resin which preferably has fine particles with a particle diameter of less than 150 mm as a main component and in which the fine particles content is more preferably 50% by weight or more and still more preferably 70% by weight or more. Since the classification efficiency of a sieve generally does not reach 100% in the industrial aspect, in a case where fine particles having a particle diameter of less than 150 mm are extracted as much as possible from particles having a particle size distribution, a sieve having a mesh size of more than 150 mm may also be used. Specifically, a sieve having a mesh size of 150 to 200 mm is used.

Further, a polymerization inhibitor is preferably contained in the water-absorbing resin fine powder. The polymerization inhibitor is preferably the same type of polymerization inhibitor as the polymerization inhibitor contained in the aqueous monomer solution. Specifically, methoxyphenols or the resembling structure thereof are preferable and p-methoxyphenol is more preferable. In addition, the concentration of the polymerization inhibitor contained in the water-absorbing resin fine powder is preferably 1 to 100 ppm, more preferably 5 to 50 ppm, and still more preferably 10 to 25 ppm.

From the viewpoint of a balance between polymerization stability of the aqueous monomer solution and color of the hydrogel-forming crosslinked polymer, it is preferable that the concentration of the polymerization inhibitor (particularly, p-methoxyphenol) contained in the aqueous monomer solution be higher than the concentration of the polymerization inhibitor (particularly, p-methoxyphenol) contained in the water-absorbing resin fine powder.

Further, at least one selected from the group consisting of polyol, alkanolamine, polyamine, and metal ions of three or higher valence is preferably contained in the water-absorbing resin fine powder.

(Transportation Step and Storing Step for Particulate Additive)

In the present invention, before the particulate additive is added to the aqueous monomer solution and/or the hydrogel-forming crosslinked polymer (that is, before the adding step), it is preferable to include a storing step for storing the particulate additive in a vessel such as a hopper and a transportation step for putting in the particulate additive to the hopper. This transportation step means a step of transporting the particulate additive from a certain point to another via a pipe or a transporting apparatus. When such a step is included, the particulate additive can be stably added to the aqueous monomer solution and/or the hydrogel-forming crosslinked polymer. For a vessel that may be used in the present invention such as a hopper, it is preferable to have a structure that blocks air outside the vessel, and preferable to have a structure that allows introducing an inert gas via a pipe or the like. Introducing an inert gas at a desired flow rate allows an oxygen concentration within a vessel such as a hopper to be at a certain value or less.

As a particulate additive, when, for example, commercially available inorganic particles or fine powder of the water-absorbing resin is used, inclusion of the transportation step is preferable for delivering the stored inorganic particles to a hopper and/or delivering the water-absorbing resin fine powder from a production point to a hopper. From the viewpoint of ease of transportation, the transportation step is preferably pneumatic conveyance.

According to the preferred embodiment of the present invention, the transportation step for transporting the particulate additive is further included before the adding step and pneumatic conveyance is performed at the transportation step.

Further, from the viewpoint of stabilizing physical properties of the water-absorbing resin to be obtained, it is preferable to include the storing step for storing the particulate additive in a vessel such as a hopper, and a particulate additive is supplied in a controllable amount from the storing step to certain other points, that is, an aqueous monomer solution preparation step, a polymerization step, and a gel-crushing step.

(Oxygen Concentration in Ambient Atmosphere)

In the producing method according to the present invention, the oxygen concentration in an ambient atmosphere of the particulate additive is set to 5% by volume or less. The oxygen concentration in an ambient atmosphere of the particulate additive should be set as low as possible. Specifically, in the relevant steps, the oxygen concentration is 5% by volume or less, preferably 4% by volume or less, more preferably 3% by volume or less, still more preferably 2% by volume or less, further still preferably 1% by volume or less, and particularly preferably 0.5% by volume or less. When the oxygen concentration is beyond 5% by volume, physical properties of the water-absorbing resin may be declined, thus not preferable. In actuality, the oxygen concentration could be about 0.01% by volume or more.

The "ambient atmosphere of the particulate additive" means a gas present in a space surrounding the particulate additive. Specifically, the ambient atmosphere of the particulate additive indicates a gas within a pipe that is used when adding the particulate additive to an aqueous monomer solution and/or a hydrogel-forming crosslinked polymer, or a gas within an empty portion exist around the particulate additive in the vessel that stores the particulate additive (storing step).

More specifically, if the step of adding a particulate additive is performed at an aqueous monomer solution preparation step, the "ambient atmosphere of the particulate additive" indicates at least one gas within a tank or a pipe for the aqueous monomer solution.

Further, if the step of adding a particulate additive is performed at the polymerization step, the "ambient atmosphere of the particulate additive" indicates a gas within a pipe for adding the particulate additive to a polymerization apparatus.

Furthermore, if the step of adding a particulate additive is performed at the gel-crushing step, the "ambient atmosphere of the particulate additive" indicates a gas within a pipe for adding the particulate additive to a gel-crusher.

"Setting the oxygen concentration in an ambient atmosphere of the particulate additive to 5% by volume or less" may be performed at any point in those steps for the method of producing the polyacrylic acid (salt)-based water-absorbing resin. For the embodiments described above, preferably, the oxygen concentration within at least one of: the pipe for adding the particulate additive to the polymerization apparatus; and the vessel for storing the particulate additive, is lowered to 5% by volume or less.

An oxygen concentration of preferably within 1 m, or more preferably within 0.5 m from a point at which an apparatus for putting in the particulate additive and a pipe are connected, is set to the above range.

The adjustment of the oxygen concentration may be performed by providing an inert gas treatment step for lowering the oxygen concentration in an ambient atmosphere of the particulate additive using an inert gas. The timing of the inert gas treatment step is preferably concurrently with and/or before the step for adding the particulate additive. In this way, the adjustment of the oxygen concentration can be performed by substitution with an inert gas.

The inert gas to be used is appropriately changed depending on the type of the particulate additive or the step of an addition destination, and examples thereof include noble gas, nitrogen, carbon dioxide, and water vapor. In a case where water-absorbing resin fine powder is used as a particulate additive, water vapor or the like is not suitable. Further, from the viewpoint of availability, the oxygen concentration in an ambient atmosphere of the particulate additive may be lowered by using preferably nitrogen or carbon dioxide and more preferably nitrogen.

According to the preferred embodiment of the present invention, a storing step for storing the particulate additive is further included before the adding step, and in the storing step, the oxygen concentration in an ambient atmosphere of the particulate additive is set to 5% by volume or less.

In addition, for adjustment of the oxygen concentration in the storing step, the same method as described above can be performed. Specifically, a method in which substitution with the inert gas is performed by introducing the inert gas to a particle layer (powder layer) in a hopper is mentioned. As a method for introducing the inert gas, the inert gas may be introduced continuously or discontinuously as long as the oxygen concentration in an ambient atmosphere of the particulate additive can be adjusted to the above range when adding the particulate additive; however, preferably, introducing the inert gas is carried out by using a discontinuous pulse-type air knocker.

As to an environment where the water-absorbing resin fine powder may be separated (for example, a classification step or a bag filter), lowering the oxygen concentration in an atmosphere in advance, that is to introduce the inert gas within such an environment may be considered. However, this may cause operations to be cumbersome or costs to increase, thus not preferable.

Further, by introducing the inert gas to a particle layer (powder layer) in a hopper, in addition to the effect of lowering the oxygen concentration, a technical effect of stabilizing the fluidity of the particulate additive in the hopper is observed. By stabilizing the fluidity, variance in the amount that has to be added over time can be minimized thereby yielding a water-absorbing resin with further improved performance.

All these are due to the fact that physical properties such as fluid retention capacity under pressure and liquid permeability can vary for various factors, which means that when water-absorbing resins with different values of such physical properties are mixed, generally, those values do not necessarily become the weighted average values. In particular, if the particulate additive is water-absorbing resin fine powder, variance in the amount to be added greatly affects a performance difference for the water-absorbing resin, making stable addition extremely important.

(Temperature of Particulate Additive)

In the present invention, the temperature of the particulate additive is increased in advance to preferably 30 to 150 C, more preferably 40 to 100 C, and still preferably 50 to 90 C by heating. In particular, when the particulate additive is water-absorbing resin fine powder, it is preferable to adjust the temperature to be within the above temperature range before addition to the aqueous monomer solution and/or the hydrogel-forming crosslinked polymer and/or before treatment with an inert gas. Further, also in the transportation step and/or the storing step, it is preferable to perform heating in advance such that the same temperature range is achieved. That is, according to the preferred embodiment of the present invention, the temperature of the particulate additive is increased to be 30 to 150 C by heating before the adding step and/or before the inert gas treatment step.

When the heating temperature is too high, the particulate additive may agglomerate, thereby losing fluidity, or when the heating temperature is too low, dew condensation may occur on the surface of the particulate additive, causing the particulate additive to adhere to each other, thereby losing fluidity. For these reasons, the heating temperature has to be set up in accordance with of the conditions of the particulate additive to be used.

(Addition Point)

In the present invention, the particulate additive is added to the aqueous monomer solution and/or the hydrogel-forming crosslinked polymer. A step having these addition points is particularly preferably the aqueous monomer solution preparation step, the polymerization step, and the gel-crushing step.

In a case where the addition point of the particulate additive is the aqueous monomer solution preparation step, a method for mixing the particulate additive with the aqueous monomer solution is not particularly limited, and a commercially available mixer can be used. However, in a case where the particulate additive is water-absorbing resin fine powder, from the viewpoint of having workability and decreasing residual monomers, since polymerization is started in a time as short as possible after mixing, therefore an in-line type mixer including a rotor and a stator is preferably used.

In a case where the addition point of the particulate additive is the polymerization step, mixing of the particulate additive with the aqueous monomer solution and/or the hydrogel-forming crosslinked polymer is not particularly limited and the mixing may be performed uniformly or non-uniformly. In a case where stirring performance of a polymerization apparatus is high, mixing is uniformly performed. In addition, in a case where the polymerization step is continuous polymerization, the effect of the present invention is further exhibited.

The addition point of the particulate additive in the polymerization step is not particularly limited and the particulate additive can be added at any stage in which the polymerization rate is 0 to 100%. From the viewpoint of the effect of the present invention, the particulate additive can be added preferably at a stage in which the polymerization rate is 0 to 99% and more preferably at a stage in which the polymerization rate is 0 to 98%.

Further, in a case where concurrently with or after the polymerization step, a gel-crushing step for gel-crushing the hydrogel-forming crosslinked polymer is included, it is preferable to perform the step for adding the particulate additive along with the gel-crushing step in order to satisfactorily mix the hydrogel-forming crosslinked polymer and the particulate additive.

As a polymerization apparatus or a gel-crusher, the apparatuses described in (2-2) Polymerization Step and (2-3) Gel-Crushing Step can be used. More preferably, it is preferable to perform the polymerization step, the gel-crushing step, and the step for adding the particulate additive in the same kneader polymerization apparatus. By performing these steps in the same kneader polymerization apparatus, the effect obtainable from the particulate additive (for example, improvement in fluid retention capacity under pressure) is further exhibited.

On the other hand, in a case where the particulate hydrogel-forming crosslinked polymer can be obtained directly from the aqueous monomer solution like a spray drop polymerization or a reversed phase suspension polymerization, the particulate additive is preferably added to any of the aqueous monomer solution and the particulate hydrogel obtainable concurrently with or after the polymerization step.

Further, in the present invention, although a method for supplying the particulate additive in a controllable amount is not particularly limited as long as a proper option is selected in accordance with the conditions of the particulate additive, those include, for example, supplying apparatuses of an electromagnetic type (such as an electromagnetic feeder), a rotary movement type (such as a screw type feeder or a rotary feeder), and an endless type (such as a belt feeder). If the particulate additive is water-absorbing resin fine powder, from the viewpoint of stable supply, rotary movement type supplying apparatuses are preferable, but especially a screw type feeder is more preferable. Powder fluidity can be increased using an inert gas such as nitrogen.

Further, as described above, since gas bubbles are contained in the water-absorbing resin obtained in the foaming polymerization, an amount of fine powder that is going to be generated increases as compared to an ordinary water-absorbing resin with no gas bubbles included. Therefore, the present invention is more preferable. That is, when there is a large amount of gas bubbles, a thickness of the resin itself in between gas bubbles decreases, and thus a crushed product with a certain size or more may not be obtained at the time of crushing or the mechanical strength of the gas bubble portion is weak so that fine powder may be generated by damage after crushing. As the amount of fine powder to be recovered increases, the amount of air incorporated also increases according to an increase in amount of fine powder. In an embodiment of the present invention, in a case where fine powder is recovered to be used as a particulate additive, because in the present invention, treatment for adjusting the oxygen concentration to a specific value or less is carried out, the above-described problem can be solved.

(2-5) Drying Step

This step is a step for drying the hydrogel obtained in the polymerization step and/or the gel-crushing step to obtain a dry polymer that has a desired solids content of the resin. The solids content of the resin c obtained from an amount lost from drying (a change in weight when 1 g of a water-absorbing resin is heated at 180 C for 3 hours), and is preferably 80% by weight or more, more preferably 85 to 99% by weight, still more preferably 90 to 98% by weight, and particularly preferably 92 to 97% by weight.

The drying method for the particulate hydrogel is not particularly limited, and examples thereof include heating drying, hot air drying, drying under reduced pressure, fluid bed drying, infrared drying, microwave drying, drum dryer drying, drying based on azeotropic dehydration with a hydrophobic organic solvent, and high humidity drying using high temperature steam. Among them, from the viewpoint of drying efficiency, hot air drying is preferable and band drying that hot air drying is performed on a through-flow belt is more preferable. The hot air drying can also be performed by, for example, a stationary hot air dryer. However, in consideration of industrial-scale implementation, band drying is preferable.

From the viewpoint of the color of the water-absorbing resin and drying efficiency, the drying temperature in the hot air drying (temperature of the hot air) is preferably 100 to 250 C and more preferably 120 to 220 C. The drying condition, such as wind speed or drying time, other than the drying temperature described above may be appropriately set in accordance with the moisture content of the particulate hydrogel used in drying or the total weight and target solids content of the resin. When the band drying is performed, various conditions described in WO 2006/100300 A, WO 2011/025012 A, WO 2011/025013 A, WO 2011/111657 A, and the like are appropriately employed.

By controlling the drying temperature and the drying time in the above-described ranges, CRC (fluid retention capacity) and Ext (water soluble component) of the water-absorbing resin to be obtained can be fallen within intended ranges (see [3] below).

(2-6) Crushing Step and Classification Step

This step is a step for crushing the dry polymer obtained in the drying step (crushing step) and adjusting the particle size to a predetermined range (classification step) to obtain water-absorbing resin powder (a particulate water-absorbing resin before surface crosslinking is performed is referred to as "water-absorbing resin powder" for the sake of convenience).

Examples of an apparatus, which is used in the crushing step of the present invention, include a high speed rotary type crusher such as a roll mill, a hammer mill, a screw mill, or a pin mill, a vibrating mill, a knuckle type crusher, and a cylindrical mixer, and these apparatuses are used in combination as necessary.

Further, a method for adjusting the particle size in the classification step of the present invention is not particularly limited, and examples thereof include sieve classification using a JIS standard sieve (JIS Z8801-1 (2000)) and air-stream classification. The adjustment of the particle size of the water-absorbing resin is not limited to the crushing step and the classification step, and can be appropriately implemented in the polymerization step (particularly, reversed phase suspension polymerization or spray drop polymerization) and other steps (for example, a granulating step) (Example: JIS standard sieve). Also in Example, a JIS standard sieve (JIS Z8801-1 (2000)) is used.

The weight average particle diameter (D50) of the water-absorbing resin powder obtained by the present invention is preferably 200 to 600 mm, more preferably 200 to 550 mm, still more preferably 250 to 500 mm, and particularly preferably 350 to 450 mm. Further, the proportion of particles having a particle diameter of less than 150 mm is preferably 10% by weight or less, more preferably 5% by weight or less, and still more preferably 1% by weight or less. The proportion of particles having a particle diameter of 850 mm or more is preferably 5% by weight or less, more preferably 3% by weight or less, and still more preferably 1% by weight or less. The lower limit value of proportion of these particles is also preferably low in any cases. The lower limit value is desirably 0% by weight and may be about 0.1% by weight. Further, the logarithmic standard deviation (sz) of the particle size distribution is preferably 0.20 to 0.50, more preferably 0.25 to 0.40, and still more preferably 0.27 to 0.35. These particle sizes are measured by using a standard sieve according to the measurement methods disclosed in U.S. Pat. No. 7,638,570 and EDANA ERT 420.2-02.

The aforementioned particle size is applied not only to the water-absorbing resin after surface crosslinking (hereinafter, referred to as "water-absorbing resin particles" in some cases for the sake of convenience) but also to a water-absorbing resin as a final product. For this reason, the water-absorbing resin particles are preferably subjected to surface crosslinking treatment (surface crosslinking step) so as to maintain the particle size within the aforementioned range, and it is more preferable to adjust the particle size by providing a sizing step after the surface crosslinking step.

(2-7) Surface Crosslinking Step

This step is a step for forming an area with higher crosslinking density on a surface layer (several tens of micrometers (mm) from the surface of a water-absorbing resin powder) of a water-absorbing resin powder which is obtained after the aforementioned steps, and it includes a mixing step, a heat treatment step, and a cooling step (option).

In the surface crosslinking step, a water-absorbing resin (water-absorbing resin particles) with a surface crosslinked by radical crosslinking or surface polymerization on surface of water-absorbing resin powder, by a crosslinking reaction with a surface crosslinking agent, or the like is obtained.

(Surface Crosslinking Agent)

The surface crosslinking agent to be used in the present invention is not particularly limited, and examples thereof include organic or inorganic surface crosslinking agents. Among them, from the viewpoint of physical properties of the water-absorbing resin and handleability of the surface crosslinking agent, an organic surface crosslinking agent reacting with a carboxyl group is preferable. For example, one or two or more surface crosslinking agents disclosed in U.S. Pat. No. 7,183,456 are mentioned.

The amount of the surface crosslinking agent used (if a plurality of surface crosslinking agents is used, this amount means the total amount) is preferably 0.01 to 10 parts by weight and more preferably 0.01 to 5 parts by weight per 100 parts by weight of the water-absorbing resin powder. Further, the surface crosslinking agent is preferably added in the form of an aqueous solution. In this case, the used amount of water is preferably 0.1 to 20 parts by weight and more preferably 0.5 to 10 parts by weight per 100 parts by weight of the water-absorbing resin powder. Furthermore, in a case where a hydrophilic organic solvent is used as necessary, the used amount thereof is preferably 10 parts by weight or less and more preferably 5 parts by weight or less per 100 parts by weight of the water-absorbing resin powder.

Further, additives that are added in the following "remoistening step" can be mixed with the surface crosslinking agent (aqueous solution) or added to this mixing step separately, each within a range of 5 parts by weight or less.

(Mixing Step)

This step is a step for mixing water-absorbing resin powder with the surface crosslinking agent. The mixing method of the surface crosslinking agent is not particularly limited, but examples thereof include a method in which a surface crosslinking agent solution is prepared in advance, the solution is preferably sprayed or dropped, more preferably sprayed onto the water-absorbing resin powder to mix them.

An apparatus performing the mixing is not particularly limited, but is preferably a high-speed stirring mixer and more preferably a high-speed stirring continuous mixer.

(Heat Treatment Step)

This step is a step for allowing crosslinking reaction on the surface of the water-absorbing resin powder after mixing the water-absorbing resin powder with the surface crosslinking agent.

An apparatus performing the crosslinking reaction is not particularly limited, but a paddle dryer is preferably mentioned in an actual level. The reaction temperature in the crosslinking reaction is appropriately set depending on the type of surface crosslinking agent to be used, but is preferably 80 to 250 C and more preferably 100 to 220 C.

(Cooling Step)

This step is a step which is optionally provided after the heat treatment step as necessary.

An apparatus, which performs the cooling, is not particularly limited, but the apparatus is preferably an apparatus having the same specification as that of the apparatus used in the heat treatment step and more preferably a paddle dryer. The reason for this is that by changing a heating medium to a cooling medium, a paddle dryer can be used as a cooling apparatus. The water-absorbing resin particles obtained in the heat treatment step are, as necessary, forcibly cooled preferably to 40 to 80 C and more preferably to 50 to 70 C in the cooling step.

(2-8) Remoistening Step

This step is a step for adding at least one additive, which is selected from the group consisting of a polyvalent metal salt compound, a polycationic polymer, a chelating agent, an inorganic reducing agent, and a hydroxycarboxylic compound (which are described later) to the water-absorbing resin particles obtained in the surface crosslinking step.

Since the additive is added in a form of aqueous solution or slurry, water-absorbing resin particles swell water again. Therefore, this step is referred to as "remoistening step." Further, as described above, the additive can be mixed with the water-absorbing resin powder concurrently with adding the surface crosslinking agent (aqueous solution). A moisture content of the water-absorbing resin particles is preferably controlled to a moisture content to be described later, particularly controlled to a moisture content of 2 to 9% by weight.

(Polyvalent Metal Salt and/or Cationic Polymer)

In the present invention, from the viewpoint of water absorption speed, liquid permeability, fluidity after absorbing moisture, and the like of the water-absorbing resin to be obtained, a polyvalent metal salt and/or a cationic polymer is preferably added.

Specifically, as the polyvalent metal salt and/or the cationic polymer, compounds that are disclosed in "[7] Polyvalent metal salt and/or cationic polymer" of WO 2011/040530 and the used amount thereof are applied to the present invention.

(Chelating Agent)

In the present invention, from the viewpoint of color (prevention of coloring), prevention of deterioration, and the like, of the water-absorbing resin to be obtained, a chelating agent is preferably added.

As the chelating agent, specifically, compounds and the amount of those used disclosed in "[2] Chelating Agent" of WO 2011/040530 are applied to the present invention.

(Inorganic Reducing Agent)

In the present invention, from the viewpoint of color (prevention of coloring), prevention of deterioration, reduction in the residual monomer, and the like, of the water-absorbing resin to be obtained, an inorganic reducing agent is preferably added.

As the inorganic reducing agent, specifically, compounds and the amount of those used disclosed in "[3] Inorganic Reducing Agent" of WO 2011/040530 are applied to the present invention.

(a-Hydroxycarboxylic Compound)

In the present invention, from the viewpoint of color (prevention of coloring) of the water-absorbing resin to be obtained, an a-hydroxycarboxylic compound is preferably added. The "a-hydroxycarboxylic compound" is a carboxylic acid or a salt thereof that has a hydroxyl group in the molecule thereof, and is a hydroxycarboxylic acid having a hydroxyl group in the a position thereof.

As the a-hydroxycarboxylic compound, specifically, compounds and the amount of those used disclosed in "[6] a-Hydroxycarboxylic Compound" of WO 2011/040530 are applied to the present invention.

(2-9) Step for Adding Other Additives

In the present invention, in order to provide various functions for the water-absorbing resin, an additive besides the above-described additives can also be added. Specifically, examples of the additive include a surfactant, a compound having a phosphorus atom, an oxidizer, an organic reducing agent, water-insoluble inorganic fine particles, organic powder such as a metal soap, a deodorant agent, an antibacterial agent, pulp, and a thermoplastic fiber. A compound disclosed in WO 2005/075070 as the surfactant and a compound disclosed in "[5] Water-Insoluble Inorganic Fine Particles" of WO 2011/040530 as the water-insoluble inorganic fine particles are applied to the present invention.

The amount of the additive used (added) is appropriately determined in accordance with the application of the water-absorbing resin to be obtained and thus is not particularly limited. The amount used is preferably 3 parts by weight or less, and more preferably 1 part by weight or less, per 100 parts by weight of the water-absorbing resin powder. Further, the additive can be added in any of processes for production of the polyacrylic acid (salt)-based water-absorbing resin.

(2-10) Other Steps

In the present invention, in addition to the aforementioned steps, it is possible to provide, as necessary, a granulating step, a sizing step, a fine powder removing step, a fine powder reusing step, or the like. In addition, it is possible to further include one, two or more of the steps such as a transportation step (of the water-absorbing resin), a storing step (of the water-absorbing resin), a packaging step, and a reserving step. The "sizing step" includes a fine powder removing step after the surface crosslinking step or a step for aggregating the water-absorbing resin, and in a case where the size of the aggregated resin exceeds a desired size, classifying, as necessary, and crushing the water-absorbing resin. Further, the "fine powder reusing step" includes an embodiment of adding fine powder without any change or a step for forming fine powder in a large hydrogel in any of processes for production of the water-absorbing resin.

[3] Physical Properties of Polyacrylic Acid (Salt)-Based Water-Absorbing Resin

In a case where the polyacrylic acid (salt)-based water-absorbing resin obtained by the producing method according to the present invention is used for a hygiene product, particularly, a disposable diaper, it is desirable to control at least one of physical properties presented in the following (3-1) to (3-10), preferably two or more of physical properties including AAP, more preferably three or more of physical properties including AAP, and most preferably all of physical properties to a desired range. When these physical properties satisfy the following ranges, the effect of the present invention can be sufficiently obtained and sufficient performance may be exhibited even in a high concentration disposable diaper.

Further, the polyacrylic acid (salt)-based water-absorbing resin obtained in the producing method according to the present invention is not particularly limited to a particular shape, and is preferably in a particulate form. The following description will discuss physical properties of particulate water-absorbing resin, in accordance with a preferable aspect. The following physical properties are defined in conformity to the EDANA method, unless otherwise indicated.

(3-1) CRC (Fluid Retention Capacity without Pressure)

CRC (fluid retention capacity without pressure) of the polyacrylic acid (salt)-based water-absorbing resin obtained by the producing method according to the present invention is usually 5 g/g or more, preferably 15 g/g or more, and more preferably 25 g/g or more. The upper limit value is not particularly limited and a higher value is preferable; however, from the viewpoint of balance with other physical properties, the upper limit value is preferably 70 g/g or less, more preferably 50 g/g or less, and still more preferably 40 g/g or less.

In a case where CRC is less than 5 g/g, the absorbency is low and such a water-absorbing resin is not suitable for an absorbent material for hygiene products such as disposable diapers. Further, in a case where CRC is more than 70 g/g, a speed of absorbing, for example, body fluids such as urine or blood is decreased, and thus such a water-absorbing resin is not suitable for a disposable diaper or the like whose water absorption speed is high. CRC can be controlled with the use of an internal crosslinking agent, a surface crosslinking agent, or the like.

(3-2) AAP (Fluid Retention Capacity Under Pressure)

AAP (fluid retention capacity under pressure) of the polyacrylic acid (salt)-based water-absorbing resin obtained by the producing method according to the present invention is preferably 20 g/g or more and more preferably 22 g/g or more. From the viewpoint of preventing leakage from the water-absorbing resin under load caused by the weight of a wearer when the water-absorbing resin is used for disposable diapers or the like, AAP is particularly preferably 23 g/g or more, more particularly preferably 24 g/g or more, and most preferably 25 g/g or more. The upper limit value is not particularly limited, but is preferably 30 g/g or less.

In a case where AAP is less than 20 g/g, an amount of liquid returned (generally referred to as "Re-Wet") when a pressure is applied to the absorbent material becomes large, and such a water-absorbing resin is not suitable for an absorbent material for hygiene products such as disposable diapers. Incidentally, AAP can be controlled by adjusting particle size, by the use of a surface crosslinking agent, or the like.

(3-3) Particle Size (Particle Size Distribution, Weight Average Particle Diameter (D50), Logarithmic Standard Deviation (sz) of Particle Size Distribution)

The particle size (particle size distribution, weight average particle diameter (D50), logarithmic standard deviation (sz) of particle size distribution) of the polyacrylic acid (salt)-based water-absorbing resin obtained by the producing method according to the present invention is controlled to be the same as the particle size of the water-absorbing resin powder before the surface crosslinking is performed.

(3-4) Ext (Water Soluble Component)

Ext (water soluble component) of the polyacrylic acid (salt)-based water-absorbing resin obtained by the producing method according to the present invention is usually 50% by weight or less, preferably 35% by weight or less, more preferably 25% by weight or less, and still more preferably 15% by weight or less. The lower limit value is not particularly limited, but is preferably 0% by weight and more preferably about 0.1% by weight.

From the viewpoint of providing a water-absorbing resin which has high gel strength and excellent liquid permeability, Ext is preferably 50% by weight or less. When Ext is 50% by weight or less, the re-wet is suppressed, and such a water-absorbing resin is suitable for an absorbent material for hygiene products such as disposable diapers. Ext can be controlled by the use of an internal crosslinking agent, or the like.

(3-5) Moisture Content

The moisture content of the polyacrylic acid (salt)-based water-absorbing resin obtained by the producing method according to the present invention is preferably more than 0% by weight but 15% by weight or less, more preferably 1 to 13% by weight, still more preferably 2 to 10% by weight, and particularly preferably 2 to 9% by weight.

By controlling the moisture content to fall within the above-described range, it is possible to obtain the water-absorbing resin which is excellent in powder characteristic (for example, fluidity, transportability, or damage resistance).

(3-6) Residual Monomer

From the viewpoint of reducing odor of the water-absorbing resin and achieving stability, the residual monomer contained in the polyacrylic acid (salt)-based water-absorbing resin obtained by the producing method of the present invention is preferably 350 ppm or less, more preferably 320 ppm or less, and still more preferably 300 ppm or less. The lower limit value is not particularly limited, but is practically about 0 ppm or about 10 ppm.

When the residual monomer content is more than 350 ppm, there is a problem of odor, which is considered to be derived from the residual monomer, of the water-absorbing resin.

(3-7) SFC (Saline Flow Conductivity)

SFC (saline flow conductivity) of the polyacrylic acid (salt)-based water-absorbing resin obtained by the producing method according to the present invention is preferably $50 \cdot 10^{-7}$ cm$^3$ s g$^{-1}$ or more, more preferably $60 \cdot 10^{-7}$ cm$^3$ s g$^{-1}$ or more, still more preferably $70 \cdot 10^{-7}$ cm$^3$ s g$^{-1}$ or more, and particularly preferably $80 \cdot 10^7$ cm$^3$ s g$^1$ or more. The upper limit value is not particularly limited, but is preferably $3000 \cdot 10^{-7}$ cm$^3$ s g$^{-1}$ or less and more preferably $2000 \cdot 10^{-7}$ cm$^3$ s g$^{-1}$ or less.

In consideration of liquid permeability of body fluids such as urine or blood as an absorbent material for hygiene products such as disposable diapers, SFC is preferably $50 \cdot 10^7$ cm$^3$ s g$^{-1}$ or more. Further, from the viewpoint of sufficiently absorbing body fluids such as urine or blood as absorbent material for hygiene products such as disposable diapers and preventing liquid leakage, SFC is preferably $3000 \cdot 10^{-7}$ cm$^3$ s g$^{-1}$ or less. SFC can be controlled by adjusting particle size, by the use of a surface crosslinking agent, a polyvalent metal salt, or a cationic polymer, or the like.

(3-8) FSR (Water Absorption Speed)

FSR (water absorption speed) of the polyacrylic acid (salt)-based water-absorbing resin obtained by the producing method according to the present invention is preferably 0.25 g/g/s or more, more preferably 0.28 g/g/s or more, still more preferably 0.30 g/g/s or more, and particularly preferably 0.32 g/g/s or more. The upper limit value is not particularly limited, but is preferably 5.0 g/g/s or less and more preferably 3.0 g/g/s or less.

From the viewpoint of sufficiently absorbing body fluids such as urine and blood as absorbent material for hygiene products such as disposable diapers and preventing liquid leakage, FSR is preferably 0.25 g/g/s or more. FSR can be controlled by polymerization while a particulate additive is added or foaming polymerization, by adjusting particle size, or the like.

According to the preferred embodiment of the present invention, in order to decrease the irritating nature when the water-absorbing resin is used as a disposable diaper, FSR of the polyacrylic acid (salt)-based water-absorbing resin is 0.25 g/g/s or more and the residual monomer of the polyacrylic acid (salt)-based water-absorbing resin is 350 ppm or less.

[4] Use of Polyacrylic Acid (Salt)-Based Water-Absorbing Resin

The use of the polyacrylic acid (salt)-based water-absorbing resin obtained by the producing method according to the present invention is not particularly limited, and is preferably used as an absorbent material for hygiene products such as disposable diapers, sanitary napkins, and incontinence pads. In particular, the polyacrylic acid (salt)-based water-absorbing resin can be used as an absorbent material of a high concentration disposable diaper (in which a large use amount of water-absorbing resin is contained in one disposable diaper) that conventionally had a problem such as an odor derived from a raw material and coloration. Further, in a case where the polyacrylic acid (salt)-based water-absorbing resin is used in an upper layer part of the absorbent material, remarkable effects can be expected.

Further, as the absorbent material, an absorbent material such as pulp fibers can also be used in addition to the water-absorbing resin. In this case, the water-absorbing resin content (core concentration) in the absorbent material is preferably 30 to 100% by weight, more preferably 40 to 100% by weight, still more preferably 50 to 100% by weight, further still more preferably 60 to 100% by weight, particularly preferably 70 to 100% by weight, and most preferably 75 to 95% by weight.

By controlling the core concentration to fall within the above-described range, in a case where the absorbent material is used in an upper layer part of an absorbent article, the absorbent article can maintain its white color state with clean and fresh look. Further, such an absorbent material is excellent in diffusion property with respect to, for example, body fluids such as urine and blood, and it is therefore expected to have an increased absorption amount by efficient liquid distribution.

In the method for producing a polyacrylic acid (salt)-based water-absorbing resin of the present invention, when a particulate additive is effectively added during the production of the water-absorbing resin, the residual monomer in the water-absorbing resin after drying can be suppressed with such a configuration, and absorbent performance is stabilized.

EXAMPLES

Hereinafter, the present invention will be described in more detail by means of Examples and Comparative Examples; however, the present invention is not intended to be limited thereto. Examples obtained by properly combining technical means disclosed in each Example are also included in the technical scope of the present invention.

The power source of an electrical apparatus used in Examples and Comparative Examples (including measurement of physical properties of the water-absorbing resin) was 200 V or 100 V, unless specifically described otherwise. In addition, various physical properties of the water-absorbing resin of the present invention were measured under conditions including room temperature (20 to 25 C) and a relative humidity of 50% RH-10%, unless specifically described otherwise.

Furthermore, in some cases, "liter" may be described as "l" or "L", and "% by weight" may be described as "wt %" for the sake of convenience.

[Measurement of Physical Properties of Water-Absorbing Resin]

(a) CRC (Fluid Retention Capacity without Pressure)

CRC (fluid retention capacity without pressure) of the water-absorbing resin of the present invention was measured according to the EDANA method (ERT 441.2-02).

(b) AAP (Fluid Retention Capacity Under Pressure)

AAP (fluid retention capacity under pressure) of the water-absorbing resin of the present invention was measured according to the EDANA method (ERT 442.2-02). The load condition was changed to 4.83 kPa (0.7 psi).

(c) Particle Size (Particle Size Distribution, Weight Average Particle Diameter (D50), and Logarithmic Standard Deviation (sz) of Particle Size Distribution)

The particle size (particle size distribution, weight average particle diameter (D50), and logarithmic standard deviation (sz) of particle size distribution) of the water-absorbing resin of the present invention was measured according to "(3) Mass-Average Particle Diameter (D50) and Logarithmic Standard Deviation (sz) of Particle Diameter Distribution" described in columns 27 and 28 of U.S. Pat. No. 7,638,570.

(d) Ext (Water Soluble Component)

Ext (water soluble component) of the water-absorbing resin of the present invention was measured according to the EDANA method (ERT 470.2-02).

(e) Residual Monomers

The residual monomers contained in the water-absorbing resin of the present invention were measured according to the EDANA method (ERT 410.2-02).

(f) FSR (Water Absorption Speed)

FSR (water absorption speed) of the water-absorbing resin of the present invention was measured according to the measurement method disclosed in WO 2011/078298.

(g) Oxygen Concentration

By using a commercially available oxygen concentration meter, the oxygen concentration at a desired point was measured. As the oxygen concentration meter, an oxygen concentration meter manufactured by NEW COSMOS ELECTRIC CO., LTD. (XP-3180) was used. Further, by appropriately disposing a nozzle at a pipe, and then inserting a detecting unit of the oxygen concentration meter to the nozzle, the oxygen concentration in a pipe was measured. Correction was carried out according to atmospheric pressure at a measurement point. It is noted that the oxygen concentration meter manufactured by NEW COSMOS ELECTRIC CO., LTD. is generally used as an oxygen concentration meter. For this reason, in a case where "the oxygen concentration in an ambient atmosphere of the particulate additive" is measured by another general oxygen concentration meter and the measured value is 5% by volume or less, it is speculated that the requirement "the oxygen concentration in an ambient atmosphere of the particulate additive is set to 5% by volume or less" is satisfied.

Production Example 1: Preparation of Particulate Additive

An aqueous monomer solution (1) having a monomer concentration of 38% by weight, a rate of neutralization of 75% by mol, and a liquid temperature of 20 C was prepared by mixing acrylic acid (containing 70 ppm by weight of p-methoxyphenol), 48% by weight of aqueous sodium hydroxide solution, ion-exchanged water, and polyethylene glycol diacrylate (n=9) (containing 100 ppm by weight of p-methoxyphenol). The used amount of the polyethylene glycol diacrylate was 0.08% by mol with respect to the monomer.

Next, the aqueous monomer solution (1) was supplied dropwise at 100 kg/hr to a continuous kneader polymerization apparatus with 60 L volume. At this time, first, the aqueous monomer solution (1) was degassed by blowing nitrogen gas at 5 L/hr to the pipe through which the aqueous monomer solution (1) was supplied to the continuous kneader polymerization apparatus, 3% by weight of aqueous sodium persulfate solution was added at 2 L/hr to be mixed with a static mixer, and then the mixture was supplied to the continuous kneader polymerization apparatus. Further, 1% by weight of aqueous L-ascorbic acid solution was added at 0.2 kg/hr from the vicinity of a supply port for a raw material (aqueous monomer solution) of the continuous kneader polymerization apparatus. Sodium persulfate is 0.059% by mol with respect to the monomer and L-ascorbic acid was 0.0027% by mol with respect to the monomer.

The continuous kneader polymerization apparatus has a form in which a jacket is disposed in the continuous kneader polymerization apparatus, and heating is performed by allowing warm water (for example, warm water at 60 C) to pass through the jacket. Further, a space of the polymerization apparatus is reduced in pressure by evacuation of air, and the pressure was -2 kPa in terms of gauge pressure.

Polymerization was started 30 seconds after the aqueous monomer solution (1) was supplied to the continuous kneader polymerization apparatus. Thereafter, a polymerization thereof was proceeded with horizontal movement so that it became a hydrogel-forming crosslinked polymer (1). With regard to the temperature during polymerization period, the maximum temperature indicated 110 C almost in the center portion of the continuous kneader polymerization apparatus.

Thereafter, polymerization reaction was terminated by performing aging for 15 minutes in the continuous kneader polymerization apparatus and then the hydrogel (1) was discharged. The temperature of the hydrogel (1) at this time was 80 C.

Next, the hydrogel (1) obtained by polymerization was dried for 40 minutes using a stationary hot air dryer with temperature 180 C and wind speed 1.5 m/sec to thereby obtain a dry polymer (1).

Subsequently, the dry polymer (1) was lightly disentangled, crushed with a roll mill, and classified using JIS standard sieves having a mesh size of 850 mm and 150 mm. By the classification, particles remaining on the sieve having a mesh size of 850 mm (hereinafter, referred to as "material on top of the sieve") (1) and particles passing through the sieve having a mesh size of 150 mm (hereinafter, referred to as "material passed though the sieve") (1) were obtained.

The material on top of the sieve (1) was 1% by weight with respect to the entire dry polymer (1) and the material passed thorough the sieve (1) was 9% by weight with respect to the entire dry polymer (1). In the following Examples, the material passed though the sieve (1) is referred to as a water-absorbing resin fine powder (A). P-methoxyphenol in the water-absorbing resin fine powder (A) was 15 ppm.

Example 1: Preparation of Polyacrylic Acid (Salt)-Based Water-Absorbing Resin

First, an apparatus used for production of a polyacrylic acid (salt)-based water-absorbing resin will be described.

As illustrated in FIG. 1, a stainless steel vessel 9 with 10 L volume is disposed at the upper side of a continuous kneader polymerization apparatus 2. A pipe 1 for supplying an aqueous monomer solution is connected to the continuous kneader polymerization apparatus 2. Further, the vessel 9 is connected to the continuous kneader polymerization apparatus 2 via a pipe 4. The connection point was positioned at a position corresponding to 25% of the entire length from the front side of the continuous kneader polymerization apparatus 2 (the side of a hydrogel discharge port 3 is defined as "rear side"). Further, a screw type feeder 10 was disposed in the middle of the pipe 4 in order to supply the contents (water-absorbing resin fine powder (A)) of the vessel 9 to the continuous kneader polymerization apparatus 2.

Further, a pipe 11b for blowing nitrogen gas to the contents (water-absorbing resin fine powder (A)) is disposed at the stainless steel vessel 9, and a nozzle (not illustrated) is disposed at the tip end thereof. Furthermore, a pipe 11a for blowing nitrogen gas is also disposed at the pipe 4 for connecting the vessel 9 and the continuous kneader polymerization apparatus 2, and a nozzle (not illustrated) is disposed at the tip end thereof. Further, the vessel 9 includes a branched portion, an oxygen concentration meter 13 is disposed at the inside thereof. In the pipe 4, a nozzle is also disposed at a point of 0.3 m away in the direction of the vessel 9 from the connection portion with the continuous kneader polymerization apparatus 2, and an oxygen concentration meter 12 is disposed at the inside thereof. The vessel 9, the pipe 4, and the screw type feeder 10 were heated to 70 C in advance from the outer wall using an electrical heater. However, the temperature in the branched portion in which the oxygen concentration meter is disposed was set to 40 C.

Hereinafter, specific operations will be described.

The stainless steel vessel 9 was charged with the water-absorbing resin fine powder (A) obtained in Production Example 1, and while the water-absorbing resin fine powder (A) was stored during retention time, the nitrogen gas was blown at 20 L/hr from the nozzle provided in the vessel 9 (storing step).

Further, the nitrogen gas was blown at 20 L/hr from the nozzle provided in the pipe 11a to the pipe 4 while the water-absorbing resin fine powder (A) was supplied from the stainless steel vessel 9 to the continuous kneader polymerization apparatus 2 (adding step).

The charged amount (stored amount) of the water-absorbing resin fine powder (A) in the vessel 9 during charging was controlled to be constant, 2 kg. Further, the charging was carried out by using a screw type feeder 14 in an atmosphere of dry air (temperature: 25 C, relative humidity: 20% RH).

Thereafter, while the water-absorbing resin fine powder (A) as a particulate additive was supplied to the continuous kneader polymerization apparatus 2, polymerization was performed under the same conditions as in Production Example 1.

That is, the aqueous monomer solution (1a) prepared in the same manner as in the aqueous monomer solution (1) was degassed in the same manner as in Production Example 1. Further, sodium persulfate and L-ascorbic acid were added thereto to be supplied dropwise at 100 kg/hr to the continuous kneader polymerization apparatus 2 through the pipe 1. Meanwhile, the water-absorbing resin fine powder (A) as a particulate additive was supplied to the continuous kneader polymerization apparatus 2. Thus, the polymerization step was started and preparation of a hydrogel (1a) was started.

The used amount of the water-absorbing resin (fine powder) was 10 parts by weight per 100 parts by weight of the monomer in the aqueous monomer solution. Further, a polymerization inhibitor incorporated from the acrylic acid was contained in the aqueous monomer solution, and its amount included was 57 ppm by weight.

Therefore, in the continuous kneader polymerization apparatus 2, an embodiment in which the water-absorbing resin fine powder (A) as a particulate additive is added to the aqueous monomer solution (1a) (in which polymerization had not been started yet) and/or the hydrogel (1a) was conducted, that is, the polymerization step, the gel-crushing step, and the adding step were performed in the same kneader polymerization apparatus.

By performing the operations described above, the oxygen concentration in the vessel 9 became 3% by volume (that is, the oxygen concentration in an ambient atmosphere of the water-absorbing resin fine powder (A) before being supplied to the continuous kneader polymerization apparatus 2 became 3% by volume) and the oxygen concentration (that is, the oxygen concentration in the pipe through which the water-absorbing resin fine powder (A) is supplied to the continuous kneader polymerization apparatus) in the pipe 4 (a point of 0.3 m away in the direction of the vessel 9 from a connection portion with the continuous kneader polymerization apparatus 2) was 1% by volume.

The oxygen concentration is measured at the point of 0.3 m away in the direction of the vessel 9 from the connection portion with the continuous kneader polymerization apparatus 2, but in the stationary state, the oxygen concentration in the pipe 4 may be considered to uniform. Similarly, since nitrogen gas is continuously blown at a constant flow rate, the oxygen concentration in the vessel 9 may be considered to uniform in the stationary state.

In this way as described above, a dry polymer (1a) (the solids content of the resin in the dry polymer (1a) was 95% by weight) was obtained by discharging the hydrogel (1a) through the hydrogel discharge port 3, which was prepared by performing the gel-crushing step while performing the polymerization step for polymerizing a monomer contained in the aqueous monomer solution in the presence of the water-absorbing resin fine powder (A) as a particulate additive, and drying the hydrogel in the same manner as in Production Example 1, and then the dry polymer (1a) was subjected to classification in the same manner as in Production Example 1. By the classification, a water-absorbing resin powder (1a) passing through a sieve having a mesh size of 850 mm and remaining on a sieve having a mesh size of 150 mm was obtained.

Subsequently, a surface crosslinking agent solution composed of 0.5 parts by weight of ethylene carbonate and 3 parts by weight of ion-exchanged water per 100 parts by weight of the water-absorbing resin powder (1a) obtained by the above operation was mixed using a high-speed stirring type mixer, and then was heated for 40 minutes using an airless oven set to a temperature of 205 C, thereby implementing surface crosslinking reaction.

Thereafter, by passing through a JIS standard sieve having a mesh size of 850 mm, a water-absorbing resin (1a) was obtained. The physical properties of the obtained water-absorbing resin (1a) (polyacrylic acid (salt)-based water-absorbing resin) are presented in Table 1.

The continuous kneader polymerization apparatus used for preparing the particulate additive in Production Example 1 is the same as the continuous kneader polymerization apparatus 2 in Example 1. In addition, other structures are the same as in Example 1.

Example 2: Preparation of Polyacrylic Acid (Salt)-Based Water-Absorbing Resin A water-absorbing resin (2a) was obtained by performing the same operation as in Example 1, except that blowing of nitrogen gas to the inside of the stainless steel vessel 9 was not performed and the amount of the nitrogen gas blown to the pipe 4 was changed to 40 L/hr. The physical properties of the obtained water-absorbing resin (2a) are presented in Table 1.

Further, the oxygen concentration in the vessel 9 (that is, the oxygen concentration in an ambient atmosphere of the water-absorbing resin fine powder (A) before being supplied to the continuous kneader polymerization apparatus 2) was 20% by volume, and in the pipe 4 (a point of 0.3 m away in the direction of the vessel from a connection portion with the continuous kneader polymerization apparatus) the oxygen concentration (that is, the oxygen concentration in the pipe through which the water-absorbing resin fine powder (A) is supplied to the continuous kneader polymerization apparatus) was 4% by volume.

Comparative Example 1: Preparation of Polyacrylic Acid (Salt)-Based Water-Absorbing Resin A comparative water-absorbing resin (Comparative 1a) was obtained by performing the same operation as in Example 1, except that blowing of nitrogen gas to the inside of the stainless steel vessel 9 was not performed in Example 1. The physical properties of the obtained comparative water-absorbing resin (Comparative 1a) are presented in Table 1.

Further, the oxygen concentration in the vessel 9 (that is, the oxygen concentration in an ambient atmosphere of the water-absorbing resin fine powder (A) before being supplied to the continuous kneader polymerization apparatus 2) was 20% by volume, and in the pipe 4 (that is, a point of 0.3 m away in the direction of the vessel from a connection portion with the continuous kneader polymerization apparatus) the oxygen concentration (the oxygen concentration in the pipe through which the water-absorbing resin fine powder (A) is supplied to the continuous kneader polymerization apparatus) was 7% by volume.

Comparative Example 2: Preparation of Polyacrylic Acid (Salt)-Based Water-Absorbing Resin The same operation as in Example 1 was performed, except that blowing of nitrogen gas to the inside of the stainless steel vessel and the pipe was not performed. As a result, the volatile component (for example, water vapor or acrylic acid) generated in the continuous kneader polymerization apparatus entered the inside of the pipe. Thus, the volatile component came into contact with the water-absorbing resin fine powder (A) so that clogging occurred in the pipe and thereby, it was not possible to perform stable operation.

Comparative Example 3: Preparation of Polyacrylic Acid (Salt)-Based Water-Absorbing Resin A comparative water-absorbing resin (Comparative 3a) was obtained by performing the same operation as in Example 1, except that the water-absorbing resin fine powder (A) was not supplied to the continuous kneader polymerization apparatus. The physical properties of the obtained comparative water-absorbing resin (Comparative 3a) are presented in Table 1. The pipe used at the time of supplying the water-absorbing resin fine powder (A) to the continuous kneader polymerization apparatus had been closed.

TABLE 1

| | | Oxygen concentration | | Physical properties of water-absorbing resin | | | |
|---|---|---|---|---|---|---|---|
| | Water-absorbing resin | Stainless steel vessel [vol %] | Pipe 4 [vol %] | CRC [g/g] | AAP [g/g] | FSR [g/g/s] | Residual monomer [ppm] |
| Example 1 | (1a) | 3 | 1 | 27 | 23 | 0.28 | 300 |
| Example 2 | (2a) | 20 | 4 | 27 | 23 | 0.28 | 320 |
| Comparative Example 1 | (Comparative 1a) | 20 | 7 | 27 | 22 | 0.28 | 360 |
| Comparative Example 2 | — | 20 | 19 | Clogging occurs in the pipe 4 (stable operation cannot be performed) | | | |
| Comparative Example 3 | (Comparative 3a) | — | — | 27 | 23 | 0.24 | 290 |

(Summary)

As shown in Table 1, it was found that the oxygen concentration in the storing vessel 9 and the pipe 4 influences physical properties of the water-absorbing resin. That is, it was indicated that as the oxygen concentration increases, AAP of the water-absorbing resin to be obtained tends to decrease and the residual monomers tend to increase. In addition, it was also indicated that in the embodiment that the particulate additive is not added, FSR was lowered.

Further, although the amounts of nitrogen gas used in Example 1 and Example 2 are the same, that is, 40 L/hr, a slight difference in physical properties between the water-absorbing resins to be obtained was confirmed. This phenomenon can be determined that in a case where nitrogen gas is blown to the inside of the storing vessel, the amount of oxygen incorporated to a continuous kneader polymerization apparatus is efficiently suppressed.

Figure 2:
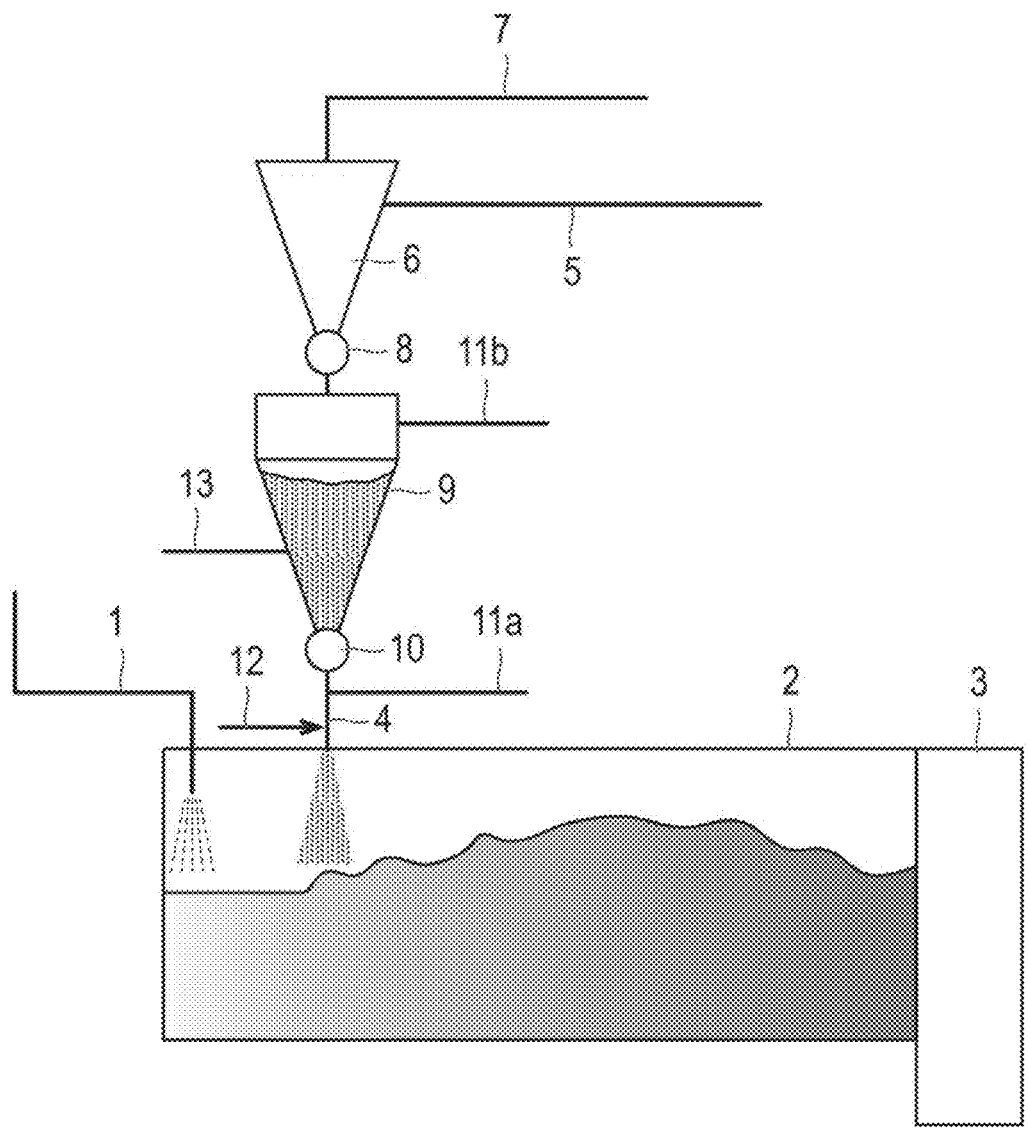
FIG. 2 is a diagram illustrating an example of an apparatus for producing a polyacrylic acid (salt)-based water-absorbing resin of the present invention.

FIG. 1 illustrates an embodiment of an apparatus of a bench level; however, as a matter of fact, the present invention is not limited thereto, and an embodiment of an apparatus of an actual level may be used. FIG. 2 is a diagram illustrating an example of an apparatus for producing a polyacrylic acid (salt)-based water-absorbing resin of the present invention. The differences will be described as follows. The vessel 9 is connected to a pneumatic conveyance line 5 for sending air to the vessel 9 and a rotary valve 8 for adjusting the air amount is disposed in the middle part. Further, a cyclone 6 is provided between the pneumatic conveyance line 5 and the rotary valve 8. This cyclone 6 plays a role of collecting water-absorbing resin fine powder floating in dry air and separating the water-absorbing resin fine powder and the dry air. The dry air separated from the water-absorbing resin fine powder is exhausted through a pneumatic conveyance exhaust pipe 7.

INDUSTRIAL APPLICABILITY

The method for producing a polyacrylic acid (salt)-based water-absorbing resin according to the present invention is preferably applied to production, in particular, large scale production, of a water-absorbing resin. In addition, the polyacrylic acid (salt)-based water-absorbing resin obtained by the present invention is excellent in use of an absorbent material for hygiene products such as disposable diapers.

REFERENCE SIGNS LIST

1 Pipe
2 Continuous kneader polymerization apparatus
3 Hydrogel discharge port
4 Pipe
5 Pneumatic conveyance line
6 Cyclone
7 Pneumatic conveyance exhaust pipe
8, 10 Rotary valve
9 Stainless steel vessel
11*a*, 11*b* Pipe
12, 13 Branched portion (oxygen concentration meter)
14, 15 Screw type feeder The present application is based on Japanese Patent Application No. 2014-40555 filed on Mar. 3, 2014, and the contents thereof are hereby incorporated by reference in its entirety into this application.

The invention claimed is:

1. A method for producing a polyacrylic acid (salt)-based water-absorbing resin, the method comprising:
    an aqueous monomer solution preparation step for preparing an aqueous solution containing a monomer having acrylic acid (salt) as a main component;
    a polymerization step for polymerizing the monomer to obtain a hydrogel-forming crosslinked polymer; and
    a drying step for drying the hydrogel-forming crosslinked polymer to obtain a dry polymer,
    wherein the method further comprises an adding step for adding a particulate additive to the aqueous monomer solution and/or the hydrogel-forming crosslinked polymer, and
    wherein, in the adding step, an oxygen concentration in an ambient atmosphere of the particulate additive is set to 5% by volume or less.

2. The method according to claim 1, further comprising a gel-crushing step for gel-crushing the hydrogel-forming crosslinked polymer concurrently with or after the polymerization step,
    wherein the adding step is performed along with the gel-crushing step.

3. The method according to claim 2, wherein the polymerization step, the gel-crushing step and the adding step are performed in a same kneader polymerization apparatus.

4. The method according to claim 1, wherein the polymerization step is performed by continuous kneader polymerization.

5. The method according to claim 1, further comprising a transportation step for transporting the particulate additive before the adding step,
    wherein at the transportation step pneumatic conveying is performed.

6. The method according to claim 1, further comprising a storing step for storing the particulate additive before the adding step,
    wherein at the storing step an oxygen concentration in an ambient atmosphere of the particulate additive is set to 5% by volume or less.

7. The method according to claim 1, further comprising an inert gas treatment step for lowering, using an inert gas, an oxygen concentration in an ambient atmosphere of the particulate additive.

8. The method according to claim 7, wherein a temperature of the particulate additive is heated to 30 to 150 C before the adding step and/or before the inert gas treatment step.

9. The method according to claim 1, wherein the particulate additive contains 0.01 to 5 parts by weight of inorganic particles per 100 parts by weight of the monomer in the aqueous monomer solution.

10. The method according to claim 1, wherein the particulate additive contains 1 to 30 parts by weight of a water-absorbing resin fine powder per 100 parts by weight of the monomer in the aqueous monomer solution.

11. The method according to claim 10, wherein the water-absorbing resin fine powder is a water-absorbing resin containing 70% by weight or more of fine particles having a particle diameter of less than 150 mm.

12. The method according to claim 10,
    wherein the aqueous monomer solution and the water-absorbing resin fine powder contain p-methoxyphenol, and
    wherein a concentration of p-methoxyphenol contained in the aqueous monomer solution is higher than a concentration of p-methoxyphenol contained in the water-absorbing resin fine powder.

13. The method according to claim 10, wherein at least one selected from the group consisting of polyol, alkanolamine, polyamine, and metal ions of three or higher valence is contained in the water-absorbing resin fine powder.

14. The method according to claim 1, wherein a FSR of the polyacrylic acid (salt)-based water-absorbing resin is 0.25 g/g/s or more, and a residual monomer of the polyacrylic acid (salt)-based water-absorbing resin is 350 ppm or less.

* * * * *